United States Patent [19]

Nichols

[11] Patent Number: 5,202,098

[45] Date of Patent: * Apr. 13, 1993

[54] MEDICAL INSTRUMENT STERILIZATION CONTAINER WITH PRESSURE INDUCED POSITIVE DRAINAGE

[76] Inventor: Robert L. Nichols, 4555 N. Jackson, Jacksonville, Tex. 75766

[*] Notice: The portion of the term of this patent subsequent to Jun. 21, 2005 has been disclaimed.

[21] Appl. No.: 682,429

[22] Filed: Apr. 8, 1991

Related U.S. Application Data

[60] Continuation-in-part of Ser. No. 505,882, Apr. 6, 1990, Pat. No. 5,080,874, which is a continuation of Ser. No. 208,730, Jun. 17, 1988, Pat. No. 4,915,918, which is a continuation of Ser. No. 821,136, Jan. 22, 1986, Pat. No. 4,752,453, which is a division of Ser. No. 668,090, Nov. 5, 1984, Pat. No. 4,617,178.

[51] Int. Cl.$^5$ .................... A61L 2/06; B65D 51/16
[52] U.S. Cl. .................... 422/300; 206/363; 206/439; 206/507; 206/508; 220/23.83; 422/292; 422/297; 422/310
[58] Field of Search ............ 422/292, 294, 297, 300, 422/310; 206/363, 439, 507, 508; 220/23.83

[56] References Cited

U.S. PATENT DOCUMENTS

| | | | |
|---|---|---|---|
| 2,342,067 | 2/1944 | Turner | 422/300 |
| 3,410,395 | 11/1968 | Sellers | 229/3.5 MF |
| 3,437,423 | 4/1969 | Mondiadis | 206/511 |
| 3,454,189 | 7/1969 | Lauterbach | 422/300 X |
| 3,697,223 | 10/1972 | Kovalcik et al. | 206/370 |
| 3,750,827 | 8/1973 | Wick | 229/3.5 MF |
| 3,890,096 | 6/1975 | Nichol et al. | 206/369 |
| 3,946,872 | 3/1976 | Stura | 229/3.5 MF |
| 4,105,407 | 8/1978 | Sanderson | 422/26 |
| 4,121,714 | 10/1978 | Daly et al. | 422/26 X |
| 4,124,141 | 11/1978 | Armentrent et al. | 220/306 |
| 4,154,342 | 5/1979 | Wallace | 206/439 |
| 4,196,166 | 4/1980 | Sanderson | 422/300 X |
| 4,210,674 | 7/1980 | Mitchell | 229/3.5 MF |
| 4,251,482 | 2/1981 | Sanderson et al. | 422/26 |
| 4,267,420 | 5/1981 | Brastad | 219/10.55 E |
| 4,359,495 | 11/1982 | Schroeder et al. | 229/3.5 MF |
| 4,402,407 | 9/1983 | Mely | 422/300 X |
| 4,416,906 | 11/1983 | Watkins | 219/10.55 E |
| 4,457,327 | 7/1984 | Pepper | 422/310 X |
| 4,458,705 | 7/1984 | Cawood | 422/300 X |
| 4,512,498 | 4/1985 | Leibinger | 422/300 X |
| 4,551,311 | 11/1985 | Lorenz | 422/300 |
| 4,752,453 | 6/1988 | Nichols | 422/300 |
| 4,915,918 | 4/1990 | Nichols | 422/300 X |
| 5,080,874 | 1/1992 | Nichols | 422/300 |

*Primary Examiner*—Jill A. Johnston
*Attorney, Agent, or Firm*—Baker & Botts

[57] ABSTRACT

A medical instrument sterilization container 90 has a housing 12, a removable tray 16 adapted for holding medical instruments and a removable lid 92. Lid 92 has no apertures or other inlets and is sealingly affixed to the housing 12 so that pressure induced positive drainage occurs providing for significantly improved drying.

16 Claims, 6 Drawing Sheets

MEDICAL INSTRUMENT STERILIZATION CONTAINER WITH PRESSURE INDUCED POSITIVE DRAINAGE

RELATED APPLICATIONS

This is a continuation-in-part application of Ser. No. 505,882 filed Apr. 6, 1990, by Robert L. Nichols entitled "Medical Instrument Sterilization Container", now U.S. Pat. No. 5,080,874, issued Jan. 14, 1992, which is a continuation application of Ser. No. 208,730, filed Jun. 17, 1988 by Robert L. Nichols entitled "Medical Instrument Sterilization Container", now U.S. Pat. No. 4,915,918, issued Apr. 10, 1990, which is a continuation application of Ser. No. 827,136, filed Jan. 22, 1986, now U.S. Patent No. 4,752,453, issued Jun. 21, 1988, to Robert L. Nichols for "Medical Instrument Sterilization Container", which is a divisional application of Ser. No. 668,090, filed Nov. 5, 1984, now U.S. Pat. No. 4,617,178 issued Oct. 14, 1986 to Robert L. Nichols for "Medical Instrument Sterilization Container".

TECHNICAL FIELD OF THE INVENTION

This invention is related to the technical field of medical instrument sterilization containers and more particularly to a medical instrument sterilization container with pressure induced positive drainage.

BACKGROUND OF THE INVENTION

Since the time Louis Pasteur discovered the germ theory of infection, medical instruments have required sterilization to prevent contamination and the spread of infection in patients. Hospitals and other medical care providers, faced with substantial numbers of instruments to be sterilized, are in constant need of ways to increase the efficiency and speed of the sterilization process. Further, not only do the hospitals need to expedite the sterilization of the instruments, but because they cannot determine exactly when the instruments will be used, they need to provide storage facilities for the instruments after the instruments have been sterilized so the instruments remain sterile.

In order to sterilize medical instruments, hospitals typically use steam sterilizers. Steam sterilizers apply a combination of heat and humidity for a pre-determined period of time to kill all pathogenic organisms found on the instruments and the container holding them. When the containerized instruments are removed from the steam sterilizer, they are sterile. In order to keep them sterile, the prior art taught to wrap them in cotton muslin fabric or a non-woven polyolefin material. The instrument wrap attempted to keep the bacteria, dirt, dust and other contaminants off the instruments so that they would be sterile when used.

Wraps have a number of disadvantages. First, they require extra labor in wrapping the instruments. Second, wraps are susceptible to contamination and do not provide for a long shelf-life. Wraps are also disadvantageous for the reasons that they neither protect delicate instruments from damage during handling nor protect the handling health care workers from sharp items wrapped inside. Wraps also have problems in terms of what is referred to as consumables. In the case of the cotton material, the wraps need to be washed and processed further which adds extra cost. In terms of the non-woven disposable materials, the wraps must be disposed of, creating problems of excess waste.

The significant disadvantages of instrument wraps led to the use of medical instrument sterilization containers. An early container introduced in the U.S. was a metal box with a filter through the top to allow entry of steam. This container, originating from the Aesculap Corporation of Germany, had numerous disadvantages in this country. Health care workers are trained to reject any medical instrument found in a container where there was evidence of moisture or water and they are taught that steam must transfer through from the top through the bottom. In the sterilization process, the moisture-laden steam contacting the cooler medical instruments condenses and forms moisture in the bottom of the container. Then during the drying process, the moisture is removed. However, in the first available containers, complete removal of the moisture was not always easily achieved resulting frequently in the rejection of the load of instruments. Another problem with the first containers resulted when the hot container was removed from the steam sterilizer with moisture-laden air trapped inside. When the container cooled, the moisture-laden air recondensed to form moisture pools in the bottom of the container. These serious disadvantages with the first containers led to the introduction of a metal container with filters in both the top and bottom.

A number of containers have been provided with filter arrangements in the top and bottom. These containers can be generalized as generally flat on top, with two filters in the lid for a "full-size" container, and generally flat on the bottom with one or more filters in the bottom. To keep the bottom filters from coming into contact with the water and moisture that collects on the bottom of the container, the filters were isolated by either a raised dam or a gutter.

An alternative container design is disclosed in U.S. Pat. No. 4,551,311 to Lorenz and which was for a period of time embodied in a container marketed by the American Sterilizer Company (AMSCO). This container had no filter in the lid, employing a shield or umbrella-like outer cover and an inner plate for permitting the entry of sterilizing gases. The bottom of the Lorenz container was sloped to a centrally located drain opening that was controlled by thermostatically controlled valve. This container had numerous disadvantages, the primary one being the reliance on a mechanical device which was prone to failure.

The problems and disadvantages of the metal sterilization containers are significantly amplified when plastic is used as the material of construction. Plastic material cannot absorb or conduct heat as rapidly or as well as metal, which significantly affects the ability of the container to dry. Early container designs that attempted to employ the Aesculap structure in a plastic container were considered absolute failures and rejected by the medical profession.

Another type of plastic container is described in patents to Sanderson, U.S. Pat. Nos. 4,196,166, 4,416,417, 4,251,482, and 4,372,921. The Sanderson container had a single opening that served both as an inlet and outlet for the sterilizing gases as well as the condensate formed in the sterilization process. The Sanderson containers relied heavily on mechanical components which were found to be significantly disadvantageous and not widely accepted.

Another requirement of the hospitals in expediting the sterilization of medical instruments is the ability to stack two or more containers—one on top of another—in the sterilizer and have them perform the sterilization process completely and dry within the standard minimum dry time, generally twenty minutes or less. The containers with exposed filters on the top and bottom were not able to be stacked in the sterilizer for the reason that condensate flowing from an upper container would collect in the lower container which would neither dry nor complete the sterilization process adequately. The only containers that could be stacked in the sterilizer—such as the Lorenz containers because of their reliance on mechanical valves—were found to be unacceptable and hospitals were then required to alternate the positioning of their containers in the sterilizer making for a much less efficient operation. Another disadvantage of containers with exposed filters in the lid is that the aperture in the lid area is the primary area in which contaminants might enter the container.

The problems and disadvantages of the prior art have for many years created a long felt and unsatisfied need for a container that would dry in less than the standard twenty minute dry time for in-hospital sterilization. Another feature that has long been sought by the art is a container designed so that multiple containers can be stacked one on top of another in the sterilizer without the upper container draining condensate into the container stacked beneath it. It is also desirable to have a medical instrument sterilization container with no moving parts and therefore more reliable. These numerous disadvantages and problems of the prior art as well as the advantageous features described above have been provided with the medical instrument sterilization container of the present invention.

SUMMARY OF THE INVENTION

In accordance with the present invention, a medical instrument sterilization container is provided. The container has a housing with sidewalls and a bottom sloped to a drain and means defining an opening for transferring the medical instruments in and out of the container. A removable lid with no apertures is provided for sealing to the means defining an opening.

In accordance with another aspect of the invention, a medical instrument sterilization container includes a housing having sidewalls, a bottom sloped to a filtered drain and means defining an opening for transferring medical instruments in and out of the container. A tray is provided for receiving the medical instruments and the housing bottom has means for positioning the tray above the filter drain. The filters are constructed of a non-woven polyolefin material and the container housing lid and tray are constructed of plastic or composite.

The technical advantage of this invention is that a container is provided that will dry faster than the normal in-hospital minimum sterilization dry time, generally twenty minutes in a vacuum type sterilizer. A plurality of containers may be stacked one on top of another without adversely affecting the ability to sterilize the instruments or to dry within the required drying times. Another technical advantage is that an upper container does not drain condensate into the container stacked below. Another technical advantage of this invention is a container provided with no moving parts that is both economical and easy to use. A further technical advantage is the elimination of the apertures through the lid which eliminates the primary point through which contaminants can enter the container.

BRIEF DESCRIPTION OF THE DRAWINGS

For a more complete understanding of the present invention, the objects and advantages thereof, reference is now made to the following description taken in connection with the accompanying drawings in which.

DETAILED DESCRIPTION OF THE INVENTION

Figure 1:
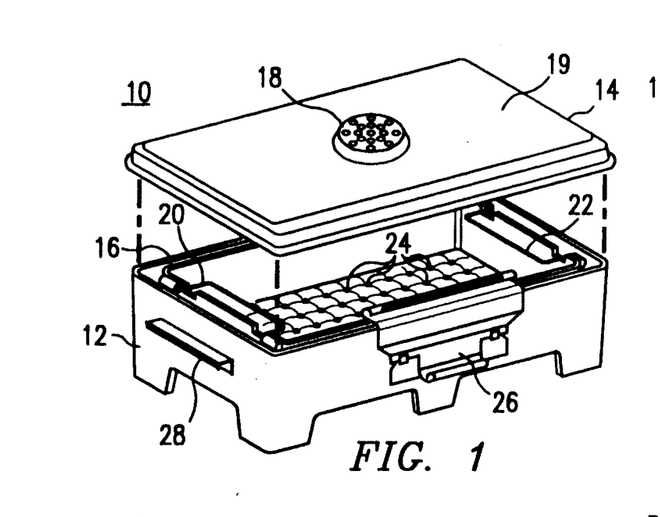
FIG. 1 is a perspective view of one embodiment of a medical instrument sterilization container showing the lid in an exploded position.

Referring to FIG. 1, the present medical instrument sterilization container is identified generally by the numeral 10 and may be seen to include the housing 12 and the removable lid 14. A removable tray 16 sits within the housing 12 and is adapted to receive various medical instruments such as knives, scissors and the like.

An inlet port 18 is disposed on lid 14 in order to allow the passage of sterilizing gases such as steam. Inlet port 18 has beneath it a filter which allows steam and sterilizing gases to pass through during the sterilization process but when dry, prevents or inhibits the passage of bacteria and other contaminants into the interior of the container. Inlet port 18 is elevated above lid surface 19 so that water or moisture generated during the sterilization process is discouraged from entering container 10. Two additional filters, to be subsequently described, are disposed in the bottom of housing 12. The tray 16 includes metal handles 20 and 22 to enable easy withdrawal of the tray 16 from the housing 12. Apertures 24 are disposed through the tray 16 to allow the passage of sterilizing gases and condensate. Metal clamps 26 are attached on both sides of the housing 12 and are manually movable in order to clamp against the lid 14 to secure the lid to secure the housing. Suitable sealing surfaces are provided between the housing 12 and the lid 14 in order to provide an essentially sealed container when the lid is clamped to the housing. Handles 28 are provided on opposite ends of container 12 to facilitate handling.

Figure 2:
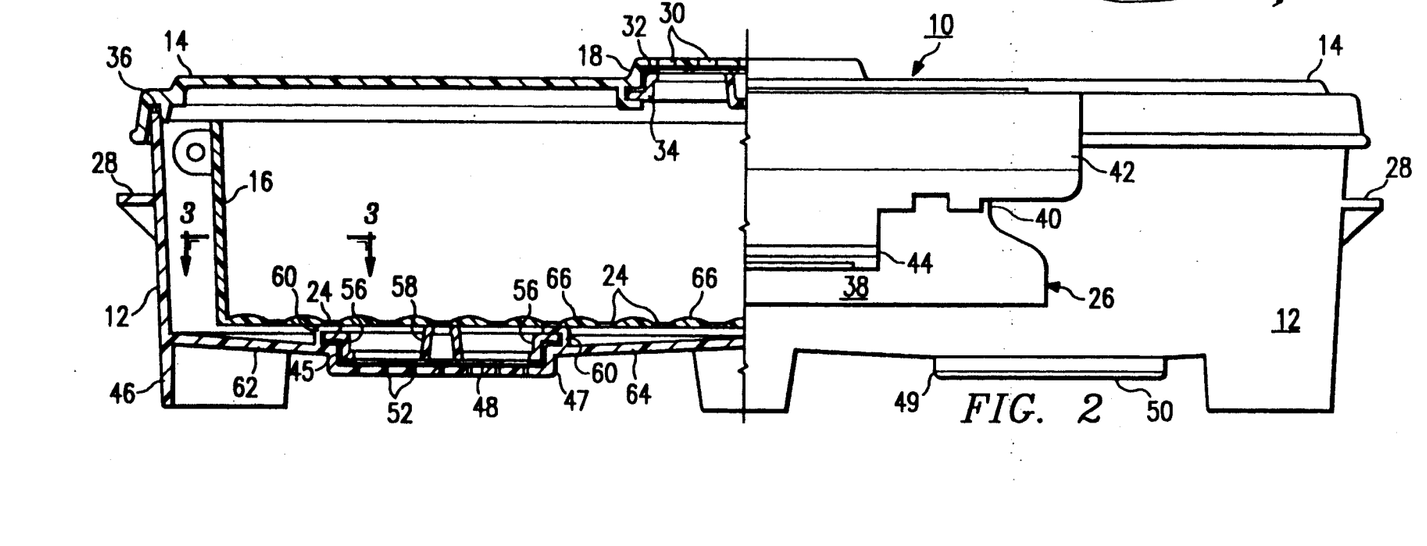
FIG. 2 is a partially sectioned view of one half of the length of the present medical instrument sterilization container shown in FIG. 1 with a front elevation thereof.

FIG. 2 illustrates a partially-sectioned view of one embodiment of the present invention shown in FIG. 1. The inlet port 18 may be seen to include apertures 30 which communicate with the atmosphere. A removable filter 32 is clamped into place by a twistable cap 34. A sealing portion 36 is illustrated between the housing 12 and the lid 14. The clamp 26 may be seen to comprise a stationary portion 38 which is pivotedly mounted by a pivot 40 to a pivotal clamp portion 42. Manual depression upon a lip 44 causes clamp 42 to be moved outwardly in order to accept the lid 14. When the lid 14 is in place, the movable clamp member 42 is moved by spring pressure to clamp against the lid in order to sealingly fix it to the housing.

FIG. 2 further illustrates pedestals 46 which elevate the bottom 45 of the housing 12. Also disposed on the bottom of the housing 12 are two outlet ports or drains 47 and 49. Contained within each of the outlet ports or drains 47 and 49 are disposable filters 48 and 50 which are constructed in a manner similar to filter 32 and in the preferred embodiment they are of the same construction. Apertures 52 are disposed through the bottom 45 of housing 12 in outlet port 47 to permit the passage of sterilizing gases and the removal of condensate. The filter 48 is held in position by twistable cap 56. A handle 58 is provided on the cap 56 to enable twisting into place. Catch members 60 inwardly extend from the bottom of the housing 12 for abutting with portions of the cap 56 in order to maintain the filter 48 securely in place.

An important aspect of the present invention is that the bottom of housing 12 slopes downwardly toward filtered outlet ports 47 and 49. Specifically, the bottom walls 62 and 64 each slope toward the location of drain 47 in different directions. Thus, condensate or moisture in the left-hand side of the tray of the housing 12 will move by gravity to the drain 47. Likewise, moisture and condensate in the right hand side of the housing 12 will move by gravity along similarly sloping housing bottom wall (not shown) to filter drain 49 (not shown).

Referring again to FIG. 2, tray 16 includes apertures 24 as previously noted. An important aspect of the present invention is that the tray bottom is configured with domes 66 and apertures 24. This domed configuration causes condensate, steam and the like, to run into the apertures 24 and prevent the accumulation of droplets of condensate or moisture on the bottom of the tray 16.

Figure 3:
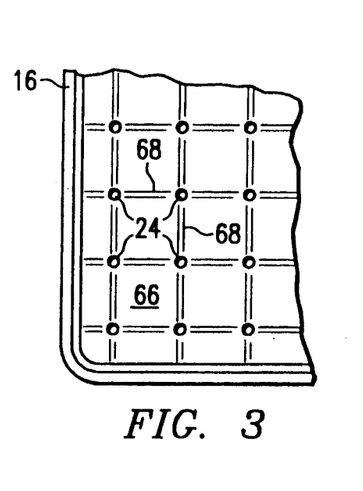
FIG. 3 is a top sectional view of a portion of the bottom of the removable tray of the invention taken along section lines 3—3 in FIG. 2.

Referring to FIG. 3, which illustrates a section of one corner of a tray 16 taken along section lines 3—3 in FIG. 2, domed portions 66 shown from a top view comprise a rectangle with an aperture 24 located at the corner thereof. The domes 66 are formed such that they slope at the corners thereof to an aperture 24. Channels 68 are formed between adjacent apertures 24 to further assist in draining condensate or moisture through the apertures 24.

Figure 4:
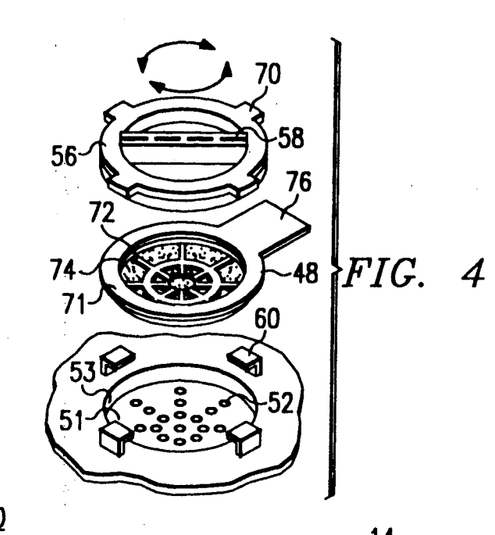
FIG. 4 is an exploded view of one of the removable filters for use in connection with the invention.

FIG. 4 illustrates in greater detail the construction of each of the filters 32, 48 and 50 and the manner of securing the filter in the inlet and outlet ports. A twistable cap 56 includes four locking flanges 70. The filters 32, 48 and 50 are circular in shape and include a plastic member 71 having plastic cross-members 72 which support the filter media 74. The filter media 74 may be any suitable type of commercially available filter which allows the passage of sterilizing gases, air, and steam therethrough but which prevents or inhibits the passage of contaminants such as dirt, dust and bacteria. Examples of available filter media include those produced and marketed by Dexter. A tab 76 extends from the filter to enable manual insertion or removal of the filter. Filters 32, 48 and 50 are removable such that they may be periodically replaced. Four locking members 60 are formed around the periphery of each port 18, 47 and 49 for receiving the filters 32, 48 and 50 and a twistable cap 56. In operation, the filters 32, 48 or 50 are placed adjacent to the cover 51 of a selected port 18, 47 or 49 and the cap 56 is twisted such that the locking flanges 70 are held within the locking members 60.

Figure 5:
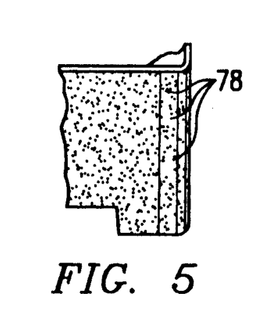
FIG. 5 is a partial view of the housing showing the mixture of high thermal conductivity material with the clear plastic.

In the preferred embodiment, the present container is formed from a suitable plastic or polymer. As previously noted, clear or translucent plastic, has a low thermal conductivity and cannot absorb enough radiant heat to eliminate condensate within the housing during the drying cycle of the sterilizer system in an economical amount of time. Consequently, the present invention contemplates the use of additional high thermal conductivity materials in conjunction with nonfilled or clear plastic in order to absorb sufficient radiant heat and subsequently rapidly radiate that heat through the container to eliminate condensate in an economical time frame. In the preferred embodiment, the present invention contemplates the mixture of high thermal conductivity materials 78 shown in FIG. 5 within the clear or translucent plastic. Alternatively, the invention contemplates the addition of a coating of high thermal conductivity materials to the clear or translucent plastic. It will be understood that various types of high thermal conductivity materials may be utilized to accomplish the object of the present invention. The following are examples which have been found to work well in practice and which provide a sterilization container having a resultant high thermal conductivity which tends to elimination the formation of condensate when used in a steam sterilizer.

EXAMPLE 1

A plastic is formed for use in a conventional plastic forming machine to provide the present container by charging a non-fluxing type high intensity mixer with polypropylene copolymer, calcium carbonate and low molecular weight polyethylene and mixing to 105 degrees centigrade. Aluminum flakes are then added and mixed for 15–20 seconds. The mixture is then fed to a single screw compounding extruder and is melt mixed at a temperature of 190 degrees to 205 degrees centigrade. The resulting polymer is then pelletized as it comes out of the extruder. The resulting copolymer pellets may be utilized in a conventional forming machine to form the present container. The formula for use with this example is listed below as a percentage by weight:

Polypropylene copolymer 55-65% approximately
Aluminum flake 35-50% approximately
Low molecular weight polyethylene 1-5% approximately
Calcium carbonate (CaCO₃) 0-15% approximately The polypropylene copolymer may comprise, for example, the copolymer manufactured by Eastman Company and noted as Tenite. Aluminum flakes may comprise the aluminum flakes manufactured by Transmet Corporation and identified as K-151. Suitable low molecular weight polyethylene is manufactured by Allied Fibers and Plastics Company as AC-9. A suitable source of calcium carbonate is Thompson, Wyman & Company under the trade name Atomite.

EXAMPLE 2

A non-fluxing type high intensity mixture is charged with polysulfone, EBS, CaCO₃ and titanate and is mixed to 150 degrees centigrade. Aluminum flakes are then added and mixed for 15 to 20 seconds. The mixture is then fed to a single screw compounding extruder and is melt mixed to a stock temperature of 250 degrees to 260 degrees centigrade. The formula for this mixture is listed below as a percentage by weight:

Polysulfone 50-60% approximately;
Aluminum flake with silane surface treatment 25-40% approximately;
(EBS) Ethylenebisstearamide 1-5% approximately;
Neoalkoxy Titanate 0.01-1% approximately;
Calcium Carbonate (CaCO₃) 1-15% approximately.

The polysulfone may comprise, for example, polysulfone manufactured by Union Carbide as Udel T-1700. A suitable neoalkoxy titanate is manufactured by Kenrich Petrochemicals under the trade name CAPOW 38/M.

EXAMPLE 3

Figure 6:
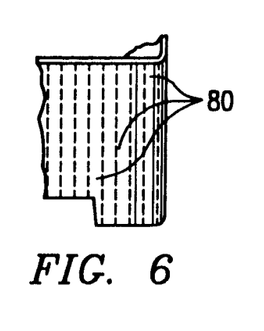
FIG. 6 is a partial view of the housing showing the high conductivity fibers mixed with the plastic.

A non-fluxing type high intensity mixture is charged with polysulfone, titanate and EBS and mixed to 150 degrees centigrade. Carbon fiber 80 shown in FIG. 6, is added and the mixture is mixed to 160 degrees centigrade. The mixture is then fed to a single-screw compounding extruder and is melt mixed at a stock temperature of 250 degrees to 260 degrees centigrade.

The formula for this mixture is set forth below as a percentage by weight:

Polysulfone 90% approximately;
Carbon fiber 10% approximately;
Neoalkoxy Titanate 0.01-1% approximately
(EBS) Ethylenebisstearamide 1-5% approximately The carbon fiber may comprise, for example, the fiber manufactured by Union Carbide Specialty Polymers and denoted as Thornel (VMD).

EXAMPLE 4

Figure 7:
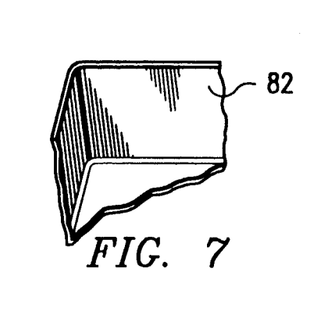
FIG. 7 is a partial view of the housing showing a high thermal conductivity material painted onto the surface thereof.

A clear or translucent plastic container is formed by one of the mixtures noted above such as polypropylene, calcium carbonate and low molecular weight polyethylene. A container is formed by conventional forming techniques and the interior of the housing and lid is then coated with semi-opaque high thermal conductivity material 78 shown in FIG. 7, such as a heat resistant paint or the like which contains carbon or the like. The container may be coated by painting, dipping or other well-known coating techniques. The clear plastic container may alternatively be impregnated with carbon pigments under pressure.

Sterilization containers formed by any of the above examples will have a relatively high thermal conductivity. For example, a thermal conductivity of polysulfone plastic is approximately 1.7 btu/hr/f²/° F./in, while the thermal conductivity of aluminum is 10.8 and carbon fiber is 60 btu/hr/f²/° F./in. Plastic containers formed in accordance with the present invention absorb substantially more heat through conduction and radiation, and therefore, heat faster and are more effective in moisture evaporation as well as more effective in killing bacteria in marginally operating steam sterilizers. The present container also enables the heat to more rapidly be transmitted to the entire interior, including the tray 16 thereby more effectively treating moisture or bacteria.

Figure 8:
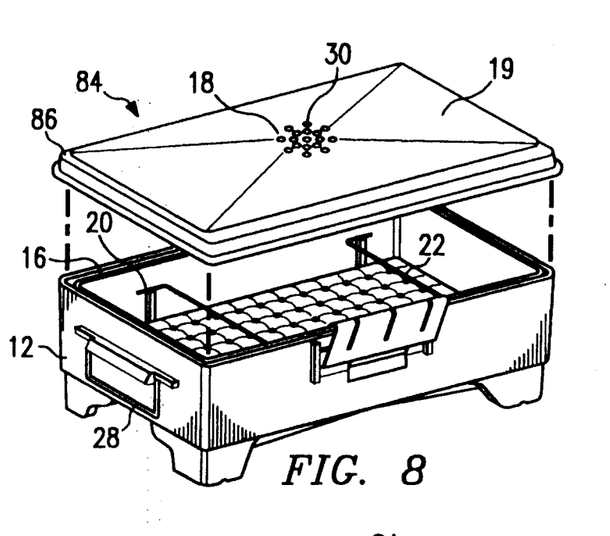
FIG. 8 is a perspective view of an alternative embodiment of a medical instrument sterilization container of the present invention showing the domed lid in an exploded position.

Referring to FIG. 8, an alternate embodiment of the medical instrument sterilization container of the present invention is shown generally at 84 and includes housing 12 and a domed removable lid 86. Inlet port 18 is disposed at the apex of the domed lid 86. When container 84 is stacked with a similar container 84 during the sterilization process, the inlet port 18 of the lower container is vertically and laterally spaced from the outlet ports 47 and 49 of the upper container such that steam or condensate exiting the upper container strikes the domed lid away from inlet port 18 of the lower container and is shed to the sides of domed lid 86. This prevents the steam or condensate from flowing into inlet 18 of the lower container of the stack and reduces pooling on the lid surface.

Figure 9:
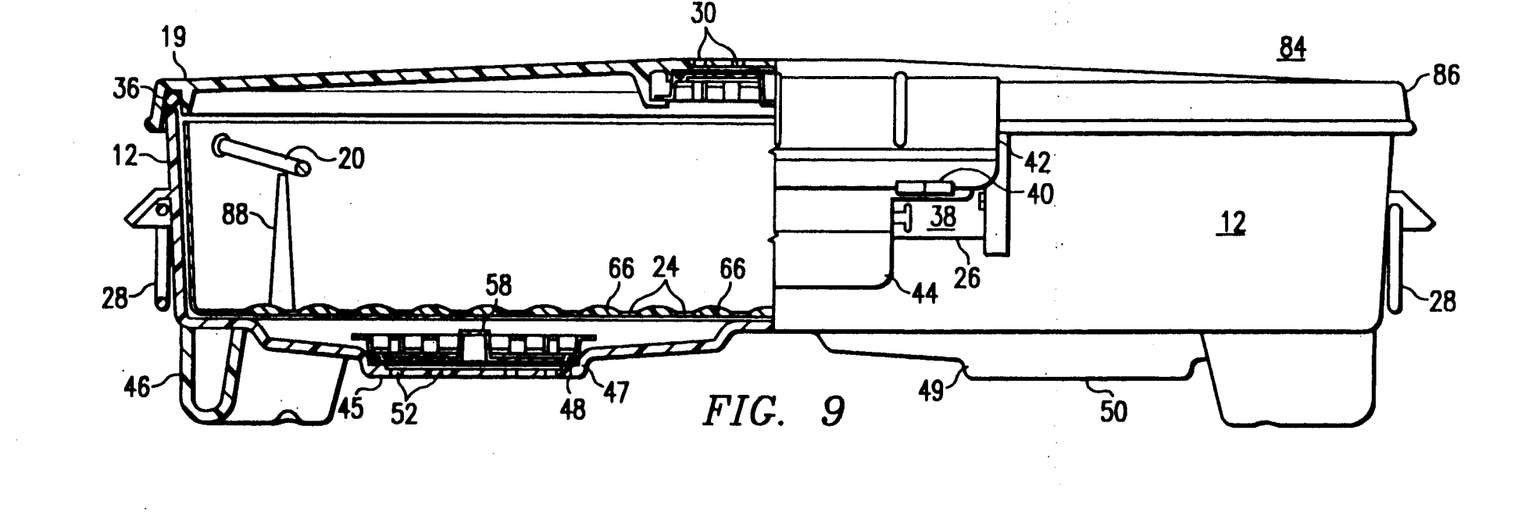
FIG. 9 is a partially sectioned view of one half of the length of the medical instrument sterilization container shown in FIG. 8 taken in connection with a front elevational view.

In the alternate embodiment 84 shown in FIG. 8 and the partially sectioned view of FIG. 9, handles 28 are pivotally mounted to the opposite ends of housing 12 to provide an improved handhold to facilitate manual transport of container 84 while at the same time minimizing space when container 84 is in storage. In a similar fashion, handles 20 and 22 of removable tray 16 are pivotally mounted to the sides of the tray to facilitate withdraw of the tray 16 from the housing 12. As indicated in FIG. 9, stops 88 are provided on the sidewalls of the tray upon which pivotally mounted handles 20 and 22 rest when not in use.

Preferably, the area over which apertures 30 are disposed across the apex of domed lid 86 is less than the respective areas over which apertures 52 are disposed across the bottom surfaces of outlet ports 47 and 49. For example, apertures 30 through lid 86 may be disposed across an area approximately half that of which apertures 52 are disposed across either outlet port 47 or outlet port 49. Such a configuration of the apertures helps expedite the removal of moisture through outlet ports 47 and 49 when a vacuum is applied to the sterilizer chamber by reducing the countervailing upward pressure applied through inlet port 18. A more complete description of this feature is discussed below, with respect to the third embodiment of the present container, which completely eliminates inlet port 18.

Figure 10:
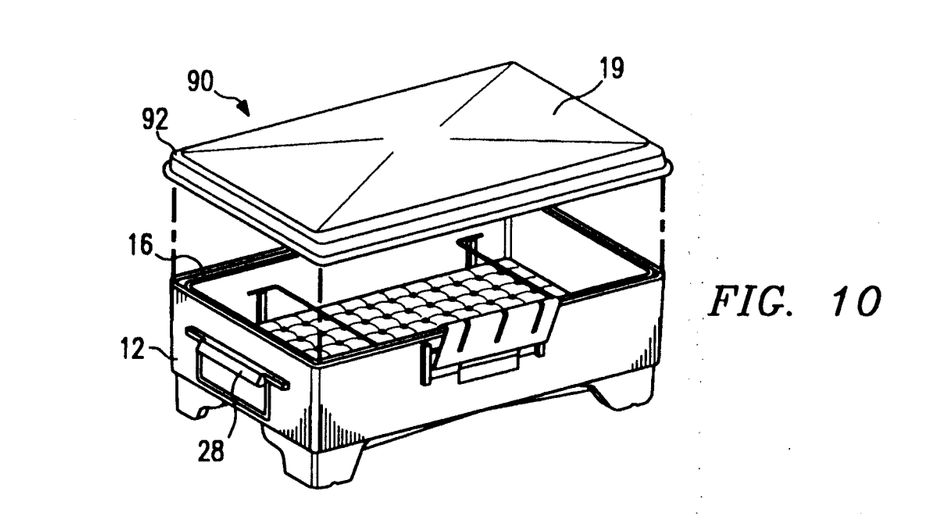
FIG. 10 is another perspective view of the preferred embodiment of the medical instrument sterilization container of the present invention showing the lid in an exploded position.
Figure 11:
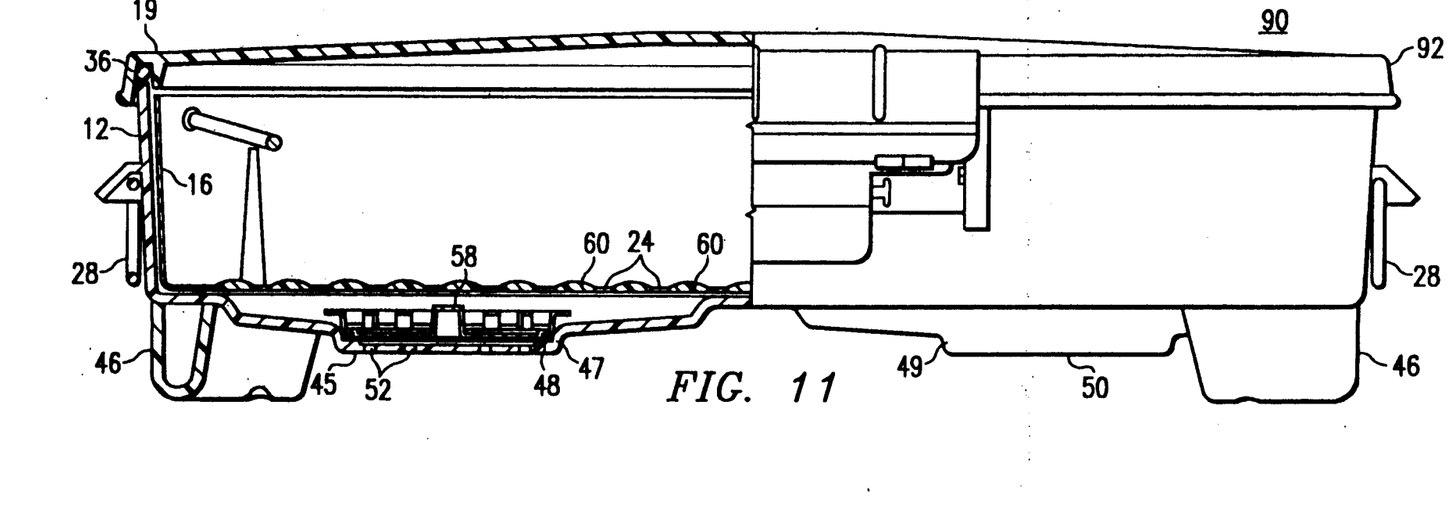
FIG. 11 is a partially sectioned view of one-half of the length of the preferred embodiment shown in FIG. 10 taken in connection with a front elevational view.

Referring next to FIGS. 10 and 11, a third alternate embodiment of the present sterilization container is shown generally at 90. Sterilization container 90 includes an entirely solid domed lid 92 that is in a sealing arrangement to housing 12. In contrast to the embodiment previously described in connection with FIGS. 1-9, sterilization container 90 is not provided with an inlet port 18, hence, no apertures 30 are disposed at the apex of lid 92. When a vacuum is applied to the sterilizer chamber to draw moisture out of container 90, the problem of countervailing forces through an inlet port 18 and the outlet ports 47 and 49 has been eliminated completely.

Figure 12:
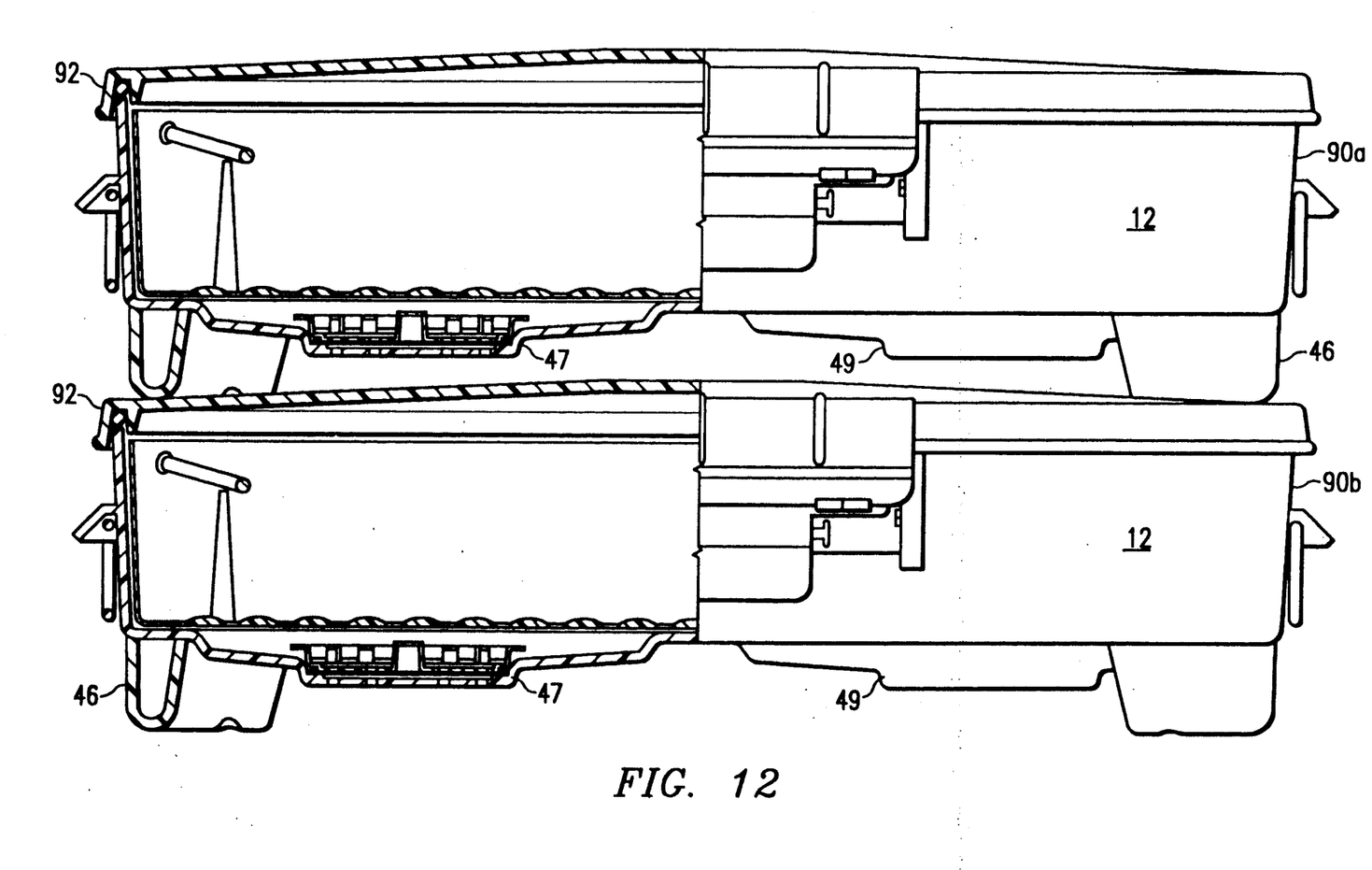
FIG. 12 shows a plurality of the containers described in the preferred embodiment stacked one on top of another.

FIG. 12 depicts a pair of stacked containers 90a and 90b. When stacked, ports 47 and 49 of the upper container are vertically offset and laterally spaced from the apex of domed lid 92 of the lower container. This stacked configuration allows sterilizing steam or gas to flow into and out of ports 47 and 49 without impediment while at the same time providing a structure in which moisture or condensate exiting ports 47 and 49 of the upper container is deflected off the lid of the lower container to the side and reduces possible pooling of moisture.

Figure 13A:
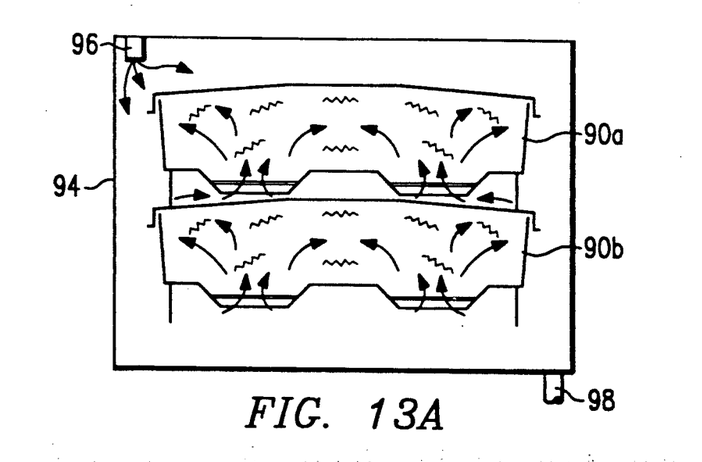
FIG. 13a-13c illustrates the operation of the container of the preferred embodiment in a steam sterilizer.
Figure 13B:
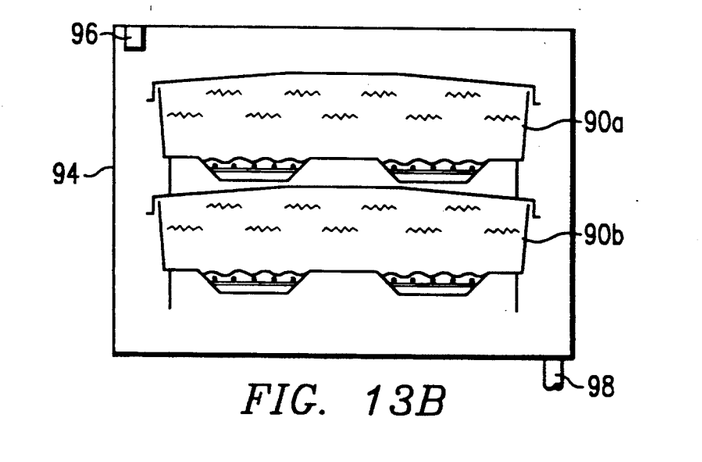
Figure 13C:
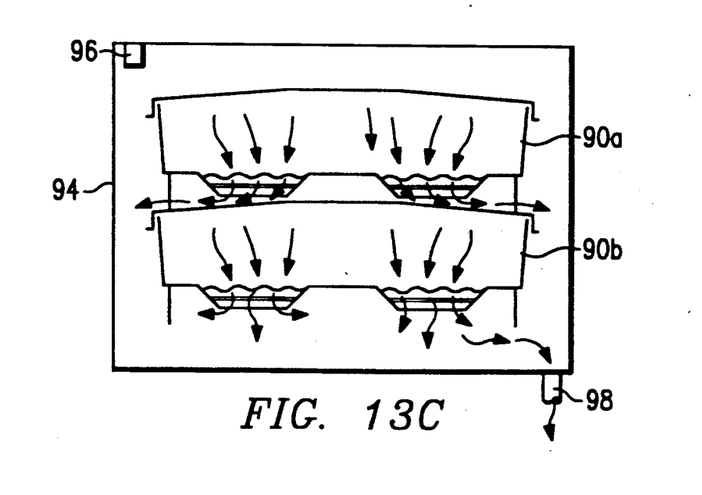

FIGS. 13a through 13c depict the use of a pair of stacked containers 90a and 90b during the sterilization process in a conventional sterilizer 94. In FIG. 13a, steam or sterilizing gas, shown generally by arrows, is injected into the chamber of sterilizer 94 through sterilizer inlet 96. Initially, the pressure in the sterilizer chamber exceeds the pressure inside containers 90a and 90b, providing the requisite pressure differential. The steam or gas then enters through ports 47 and 49 across the filter barriers provided by filters 48 and 50. Pedestals 46 provide the important function of maintaining space between the stacked containers such that the steam can enter ports 47 and 49 without substantial impediment. The steam flowing into the containers 90a and 90b sterilizes the instruments disposed therein. As the steam contacts the instruments inside the containers 90a and 90b and the sidewalls of the housings 12 of containers 90a and 90b condensate is formed.

In FIG. 13b, the pressure inside the sterilization containers 90a and 90b has equalized with the pressure in the chamber of sterilizer 94. Condensate which has formed on the sidewalls of containers 90a and 90b as well as the medical instruments disposed therein, drains to the filtered ports 47 and 49 along the sloped portions of the bottom housing 12. The condensate has a tendency to pool on the somewhat hydrophobic barrier created by filters 48 and 50 disposed in respective ports 47 and 49.

Next, as depicted in FIG. 13c, a vacuum is created within the chamber of sterilizer 94. The vacuum withdraws the condensate from containers 90a and 90b by pulling the accumulated condensate across filters 48 and 50 under vacuum pressure. The condensate exits the chamber sterilizer 94 through outlet 98. The removal of condensate across filters 48 and 50 under vacuum pressure allows for a faster and more complete drying of the instruments in the container. The elimination of an inlet port 18 through the lid eliminates countervailing upward pressure on the condensate which impedes rapid withdrawal of the condensate across filters 48 and 50.

Figures 14A, 14B:
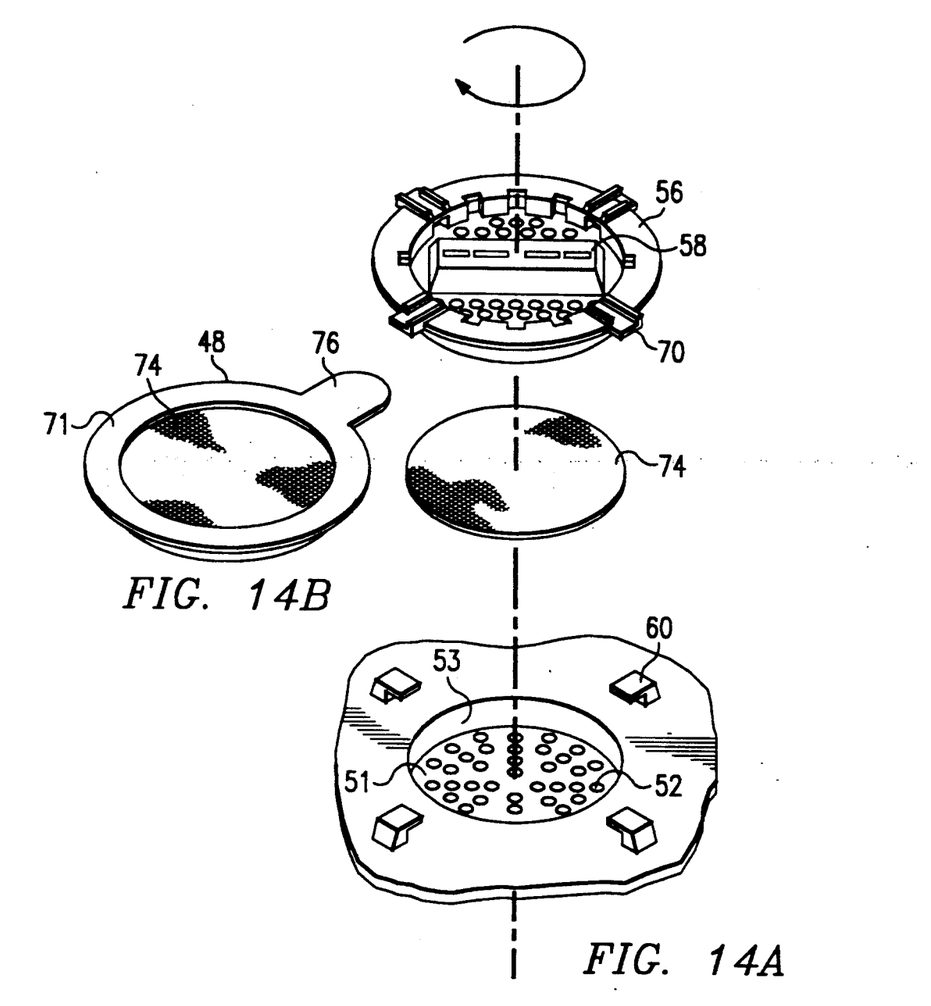
FIG. 14a-14b is an exploded view of the removable filters used in connection with a preferred embodiment.
Figure 15:
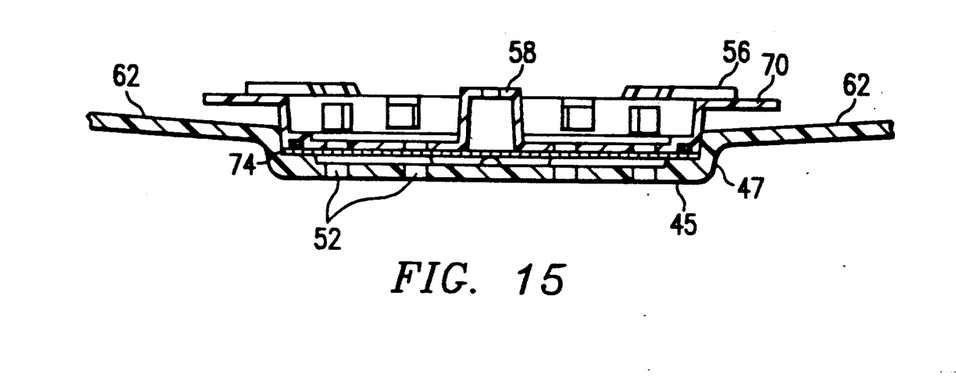
FIG. 15 is a sectional view of the removable filter shown in FIG. 14.

FIGS. 14a and 14b depict alternate approaches to filtering ports 18, 47 and 49. In the embodiment shown in FIG. 14a, filter media 74 is directly inserted into the recess of the respective port 18, 47, 49 and subsequently firmly held in place through direct contact with cap 56. A cross-sectional view of the filtering approach using filter media 74 directly inserted into the recess of the respective filter port 18, 47, 49 is shown in FIG. 15. In FIG. 14b, the filter media is again supported in plastic member 71. In this embodiment, however, the filter media 74 is supported such that when the filter 32, 48 or 50 is inserted into the recess of ports 18, 47, 49, filter media 74 is disposed between the inside of the respective container and the cross-members 72. In this configuration, the steam or sterilizing gas exiting the container is not impeded by the cross-members 72 until it has crossed the barrier provided by the filter media 74. This also facilitates more rapid removal of the condensate from the container.

Whereas the present embodiment has been described in detail, it should be understood that various changes, alterations and substitutions can be made without departing from the spirit and scope of the invention as defined by the following claims.

What is claimed is:

1. A medical instrument sterilization container comprising:
   a housing having sidewalls, a bottom sloped to a drain having a filter disposed therein and means defining an opening for transferring medical instruments in and out of said container; and
   a removable lid with no apertures therethrough for sealing to said means defining an opening.

2. The medical instrument sterilization container of claim 1 wherein said lid is dome shaped.

3. The medical instrument sterilization container of claim 1 wherein said filter is constructed of a non-woven polyolefin material.

4. The medical instrument sterilization container of claim 1 wherein said filter is constructed of a woven cotton fabric.

5. The medical instrument sterilization container of claim 1 wherein said filter is constructed of a ceramic material.

6. The medical instrument sterilization container of claim 1 wherein said container is constructed of a plastic material.

7. The medical instrument sterilization container of claim 6 wherein said plastic material is opaque.

8. The medical instrument sterilization container of claim 6 wherein said material is clear.

9. The medical instrument sterilization container of claim 6 wherein said plastic material further comprises a mixture of plastic material and another material having thermal conductivity higher than said plastic material.

10. The medical instrument sterilization container of claim 1 wherein said housing bottom slopes to two spaced apart openings.

11. The medical instrument sterilization container of claim 1 wherein said housing bottom further comprises pedestals to elevate said housing.

12. The medical instrument sterilization container of claim 1 further comprising means for positioning medical instruments out of contact with said housing bottom.

13. The medical instrument sterilization container of claim 12 wherein said means for positioning medical instruments comprises a removable tray.

14. The medical instrument sterilization container of claim 13 wherein said removable tray has a bottom with apertures therethrough and said bottom of said tray slopes toward each of said apertures.

15. A medical instrument sterilization container comprising:
   a tray for supporting medical instruments;
   a housing having a bottom sloping to a filtered drain and side walls adapted for receiving said tray; and
   a lid with no opening removably fixed to said housing.

16. A medical instrument sterilization container comprising:
   a tray for supporting medical instruments;
   a housing having side walls and a sloping bottom to a filtered opening with an area, said housing receiving said tray; and
   a removable lid with an opening therethrough having an area less than said area of said filtered opening in the bottom, said removable lid sealing an opening in said housing.

* * * * *